(12) United States Patent
Gaur et al.

(10) Patent No.: US 8,778,903 B2
(45) Date of Patent: Jul. 15, 2014

(54) MICRORNA-10 ANTAGONISTS AND MICRORNA-10 TARGETS FOR USE IN THE TREATMENT OF A GLIOMA

(75) Inventors: Arti B. Gaur, Hanover, NH (US); Mark A. Israel, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 201 days.

(21) Appl. No.: 13/502,873

(22) PCT Filed: Oct. 21, 2010

(86) PCT No.: PCT/US2010/053475
§ 371 (c)(1),
(2), (4) Date: Jul. 10, 2012

(87) PCT Pub. No.: WO2011/050129
PCT Pub. Date: Apr. 28, 2011

(65) Prior Publication Data
US 2012/0277163 A1    Nov. 1, 2012

Related U.S. Application Data

(60) Provisional application No. 61/253,670, filed on Oct. 21, 2009.

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

2002/0119945 A1    8/2002    Weinstein .................... 514/44 R
2009/0192114 A1    7/2009    Ovcharenko et al. ....... 514/44 R

OTHER PUBLICATIONS

Abdel-Fattah et al. "Differential Expression of *HOX* Genes in Neoplastic and Non-Neoplastic Human Astrocytes" Journal of Pathology 2006 vol. 209:15-24.

Chan et al. "MicroRNA-21 Is an Antiapoptotic Factor in Human Glioblastoma Cells" Cancer Research 2005 vol. 65(14):6029-6033.
Chano et al. "Identification of *RB1CC1*, a Novel Human Gene That Can Induce *RB1* in Various Human Cells" Oncogene 2002 vol. 21:1295-1298.
Ciafrè et al. "Extensive Modulation of a Set of MicroRNAs in Primary Glioblastoma" Biochemical and Biophysical Research Communications 2005 vol. 334:1351-1358.
Debernardi et al. "MicroRNA *miR-181a* Correlates with Morphological Sub-class of Acute Myeloid Leukaemia and the Expression of its Target Genes in Global Genome-wide Analysis" Leukemia 2007 vol. 21:912-916.
Gaur et al. "Characterization of MicroRNA Expression Levels and Their Biological Correlates in Human Cancer Cell Lines" Cancer Research 2007 vol. 67(6):2456-2468.
Han et al. "DNA Methylation Regulates MicroRNA Expression" Cancer Biology & Therapy 2007 vol. 6(8):1290-1294.
Hutvánger et al. "Sequence-Specific Inhibition of Small RNA Function" PLoS Biology 2004 vol. 2(4):465-475.
Ladendorff et al. "BS69, an Adenovirus E1A-Associated Protein, Inhibits the Transcriptional Activity of c-Myb" Oncogene 2001 vol. 20:125-132.
Ma et al. "Tumor Invasion and Metastasis Initiated by MicroRNA-10b in Breast Cancer" Nature 2007 vol. 449:682-688 with erratum p. 256.
Meister et al. "Sequence-specific Inhibition of Micro-RNA- and siRNA-induced RNA Silencing" RNA 2004 vol. 10:544-550.
Negrini, M. and Calin, G.A. "Breast Cancer Metastasis: A MicroRNA Story" Breast Cancer Research 2008 vol. 10(2):303-306.
Sasayama et al. "MicroRNA-10b is Overexpressed in Malignant Glioma and Associated with Tumor Invasive Factors, uPAR and RhoC" International Journal of Cancer 2009 vol. 125:1407-1413.
International Search Report from PCT/2010/053475, Dec. 28, 2010.
International Preliminary Report on Patentability from PCT/2010/053475, May 3, 2012.

*Primary Examiner* — Kimberly Chong
(74) *Attorney, Agent, or Firm* — Licata & Tyrrell P.C.

(57) ABSTRACT

The present invention embraces microRNA-antagonists and activators of homeobox D10 protein; Zinc finger, MYND domain containing 11 protein; or RB1-inducible coiled-coil 1 protein for use in decreasing glial tumor cell proliferation and treating glioma.

7 Claims, 2 Drawing Sheets

SEQUENCE LISTING

```
<160> NUMBER OF SEQ ID NOS: 4

<210> SEQ ID NO 1
<211> LENGTH: 110
<212> TYPE: RNA
<213> ORGANISM: Homo sapiens

<400> SEQUENCE: 1
gaucugucug ucuucuguau auacccugua gauccgaauu uguguaagga auuuuguggu      60
cacaaauucg uaucuagggg aauauguagu ugacauaaac acuccgcucu                110

<210> SEQ ID NO 2
<211> LENGTH: 23
<212> TYPE: RNA
<213> ORGANISM: Homo sapiens

<400> SEQUENCE: 2
uacccuguag auccgaauuu gug                                              23

<210> SEQ ID NO 3
<211> LENGTH: 110
<212> TYPE: RNA
<213> ORGANISM: Homo sapiens

<400> SEQUENCE: 3
ccagagguug uaacguuguc uauauauacc cuguagaacc gaauugugu gguauccgua       60 uagucacaga uucgauucua ggggaauaua uggucgaugc aaaaacuuca                110

<210> SEQ ID NO 4
<211> LENGTH: 23
<212> TYPE: RNA
<213> ORGANISM: Homo sapiens

<400> SEQUENCE: 4
uacccuguag aaccgaauuu gug                                              23
```

MICRORNA-10 ANTAGONISTS AND MICRORNA-10 TARGETS FOR USE IN THE TREATMENT OF A GLIOMA

INTRODUCTION

This application is a U.S. National Stage Application of PCT/US2010/053475 filed Oct. 21, 2010 and claims benefit of priority to U.S. Provisional Application Ser. No. 61/253,670, filed Oct. 21, 2010, the contents of each of which are incorporated herein by reference in their entirety.

BACKGROUND OF THE INVENTION

MicroRNAs or miRNAs are small noncoding RNAs which function by regulating target gene expression post-transcriptionally. The breadth of genetic regulatory effects potentially mediated by microRNAs and their central role in diverse cellular and developmental processes (Ambrose (2004) *Nature* 431 (7006):350-5; Bartel & Chen (2004) *Nat. Rev. Genet.* 5 (5):396-400; Miska (2005) *Curr. Opin. Genet. Dev.* 15 (5):563-8; Sevignani, et al. (2006) *Mamm. Genome* 17 (3):189-202) has lead to the suggestion that aberrant expression of microRNA genes could contribute to human disease, including cancer (McManus (2003) *Semin. Cancer Biol.* 13 (4):253-8; Caldas & Brenton (2005) *Nat. Med.* 11 (7):712-4; Lu, et al. (2005) *Nature* 435 (7043):834-8; Croce & Calin (2005) *Cell* 122 (1):6-7). A substantial number of microRNA genes are located in genomic regions that are frequently amplified, deleted, or rearranged in cancer, providing further evidence of a role for microRNAs in cancer pathogenesis (Calin, et al. (2002) *Proc. Natl. Acad. Sci. USA* 99 (24):15524-9; Nairz, et al. (2006) *Dev. Biol.* 291 (2):314-24). Deregulated microRNA expression has been documented in diverse cancers including lymphoma (Tagawa & Seto (2005) *Leukemia* 19 (11):2013-6; He, et al. (2005) *Nature* 435 (7043):828-33; Costinean, et al. (2006) *Proc. Natl. Acad. Sci. USA* 103 (18):7024-9; Kluiver, et al. (2006) *Genes Chromosomes Cancer* 45 (2):147-53 11-14), colorectal cancer (Michael, et al. (2003) *Mol. Cancer Res.* 1 (12):882-91), lung cancer (Hayashita, et al. (2005) *Cancer Res.* 65 (21):9628-32), breast cancer (Iorio, et al. (2005) *Cancer Res.* 65 (16):7065-70), and glioblastoma (Ciafre, et al. (2005) *Biochem. Biophys. Res. Commun.* 334 (4):1351-8; Chan, et al. (2005) *Cancer Res.* 65 (14):6029-33). Specific microRNAs have been shown to target genes critical for the development of cancer such as E2F (O'Donnell, et al. (2005) *Nature* 435 (7043):839-43) and RAS (Johnson, et al. (2005) *Cell* 120 (5):635-47). Hence, microRNAs and the genes they regulate can potentially provide etiologic insights as well as serve as both diagnostic markers and therapeutic targets for many different tumor types.

Gliomas are tumors that occur in the central nervous system and demonstrate invasive growth. Glioblastomas in particular are the most resistant to treatment, and have an extremely poor five-year survival rate of about 8%. Although definitive efficacy of chemotherapy has only been confirmed for alkylating agents and temozolomide, their efficacy is limited to concomitant use with radiotherapy. On the other hand, post-surgical radiotherapy has been recognized to demonstrate life-prolonging effects. Knowledge of molecular biomarkers that are associated with genetic regulatory mechanisms contributing to malignancy is essential for elucidating the mechanisms underlying malignant transformation, for understanding pathologic attributes of Glioblastoma Multiforme (GBM), and ultimately for designing effective strategies for GBM treatment. MicroRNAs encoded by the microRNA-10 gene have been identified as molecular biomarkers of GBM (Gaur, et al. (2007) *Cancer Res.* 67:2456-68; Sasayama, et al. (2009) *Int. J. Cancer* 125 (6):1407-13; Ciafre, et al. (2005) supra). In addition, mRNA expressions of RhoC and urokinase-type plasminogen activator receptor (uPAR), which were thought to be regulated by miR-10b via HOXD10 (homeobox D10), have been correlated with the expression of miR-10b, as were the protein expression levels of RhoC and uPAR (Sasayama, et al. (2009) supra).

SUMMARY OF THE INVENTION

The present invention features methods for decreasing glial tumor cell proliferation by contacting a glial tumor cell with an effective amount of a microRNA-10 antagonist, or alternatively a HoxD10 protein; ZMYND11 or RB1CC1 activator, so that the proliferation of the glial tumor cell is decreased as compared to a control. According to some embodiments, the glial tumor cell is an astrocytoma tumor cell, ependymal tumor cell, glioblastoma multiforme tumor cell, or primitive neuroectodermal tumor cell.

The present invention also embraces a method for treating glioma by administering to a subject in need thereof an effective amount of a microRNA-10 antagonist, or alternatively a HoxD10 protein; ZMYND11 or RB1CC1 activator, so that the subject's glioma is treated. In some embodiments, the glioma is an astrocytoma, ependymal tumor, primitive neuroectodermal or glioblastoma multiforme, wherein the glioblastoma multiforme is located in the brain or spinal cord of the subject, with particular embodiments embracing treatment of human subjects.

DETAILED DESCRIPTION OF THE INVENTION

Figure 1A:
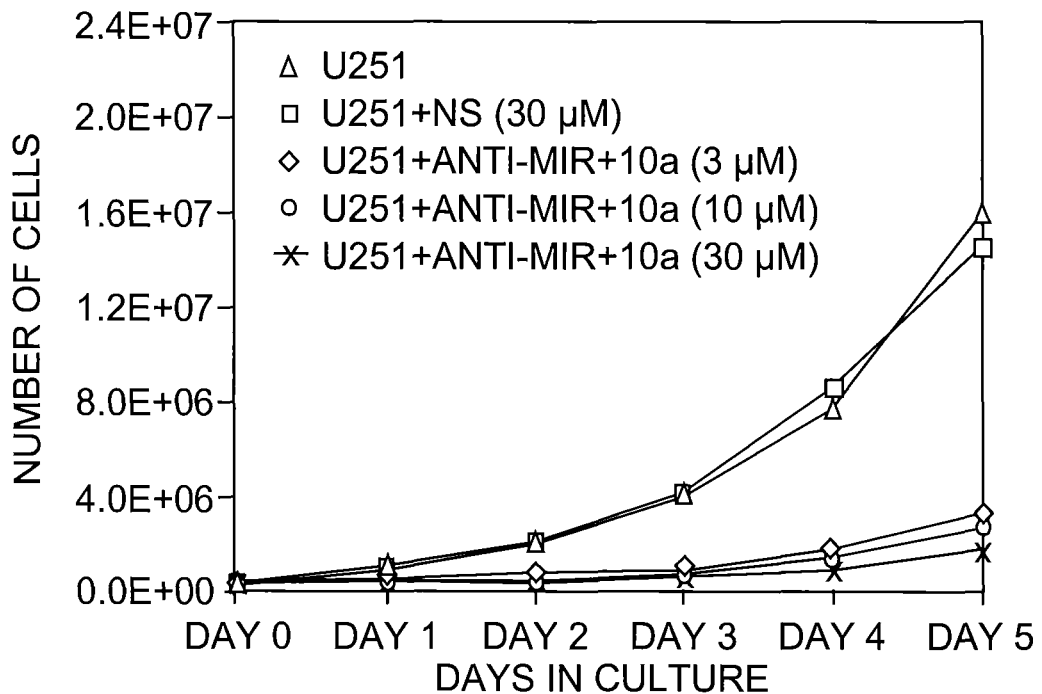
FIG. 1 shows that anti-miR-10a (FIG. 1A) or anti-miR-10b (FIG. 1B) treatment inhibits proliferation of GBM in vitro. The results represent 5 days of growth in a 10-cm tissue culture dish. Fifty thousand cells were plated on day 0 for each condition. Similar results were obtained for U87 cells cultured in either medium only, non-specific anti-mir control (30 µM), or anti-miR-10a or anti-miR-10b (3, 10 and 30 µM).

It has now been shown that down-regulation of miR-10a or miR-10b in human GBM cells leads to decreased proliferation and decreased colony formation in soft agar. Moreover, using a xenograft model in immune-deficient nude mice, down-regulation of miR-10a or miR-10b levels in human GBM cells results in decreased tumor growth in vivo. In addition, by comparing gene expression data from primary GBM and normal brain tissue with miR-10a and miR-10b levels as well as using MiRanda target prediction algorithm associated with the Sanger MIRBASE, ZMYND11 (Zinc finger, MYND domain containing 11), RB1CC1 (RB1-inducible coiled-coil 1) and HOXD10 have now been identified as targets of miR-10a and miR-10b. ZMYND11 and RB1CC1 are key regulators of the tumor suppressor RB1 (Ladendorff, et al. (2001) *Oncogene* 20(1):125-32; Chano, et al. (2002) *Oncogene* 21(8):1295-8). Regulation of HOXD10 by miR-10a and miR-10b results in increased expression of RHOC, which is known to initiate vigorous invasion of normal tissue by tumors (Negrini & Calin (2008) *Breast Cancer Res.* 10(2):

203; Ma, et al. (2007) *Nature* 449(7163):682-8). Additionally, both miR-10a and miR-10b are located within HOX clusters: miR-10a is within the HOX B cluster on 17q21 and miR-10b is in the HOX D cluster on 2q31 (Nairz, et al. (2006) supra). HOX clusters play crucial roles during normal development and in oncogenesis. HOX genes are differentially expressed in normal and GBM cell lines as well as in primary GBM tumor tissue, suggesting their potential roles as transforming genes (Abdel-Fattah, et al. (2006) *J. Pathol.* 209(1): 15-24). MicroRNAs have been shown to regulate HOX genes in acute myeloid leukemia (Garzon, et al. (2008) *Proc. Natl. Acad. Sci. USA* 105(10):3945-50). Specifically, miR-10a and miR-10b show a clear correlation with HOX gene expression (Debernardi, et al. (2007) *Leukemia* 21(5):912-6) and HOXD10 has been shown as a target of miR-10a and miR-10b (Debernardi, et al. (2007) supra; Han, et al. (2007) *Cancer Biol. Ther.* 6(8):1290-1294). As described herein, in vitro studies demonstrated that specific down-regulation of miR-10b in GBM-derived cell lines results in increased expression levels of HOXD10.

Collectively, these findings indicate that miR-10a and miR-10b, and targets thereof, are associated with pathologic characteristics of glioma. Accordingly, the present invention embraces the use of miR-10 antagonists and ZMYND11, RB1CC1 and HOXD10 activators to decrease glial tumor cell proliferation and in the treatment of glioma. In accordance with methods for decreasing glial tumor cell proliferation, a glial tumor cell is contacted with an agent that inhibits the expression or activity of a product of the microRNA-10 gene (i.e., a miR-10 antagonist), or alternatively a ZMYND11, RB1CC1 or HOXD10 activator so that tumor cell growth is decreased or inhibited as compared to a control cell, e.g., a tumor cell not contacted with said antagonist or activator. For the purposes of the present invention, a glial tumor cell is intended to mean a tumor cell of the central nervous system, including astrocytomas, ependymal tumors, glioblastoma multiforme, and primitive neuroectodermal tumors. Inhibition of glial tumor cell proliferation can be determined by routine methods (e.g., optical density, colony counts or cell counts), wherein the antagonists or activators of the invention provide at least a 20%, 30%, 40%, 50%, 60%, 70%, 80%, 90%, 95%, 98%, or 99% decrease in the number of glial tumor cells when compared to control cells. In some embodiments, the glial tumor cell is isolated and contacted in vitro. In other embodiments, the tumor cell is contacted in vivo.

Inhibition of glial tumor cell proliferation finds application in the decreasing the size of glial tumors and in the treatment of glioma. In this respect, the present invention also embraces a method for treating glioma in a subject. This method involves administering an effective amount of a miR-10 antagonist, or alternatively a ZMYND11, RB1CC1 or HOXD10 activator, to a subject in need thereof to treat the glioma.

As is conventional in the art, glioma refers to a cancer of the central nervous system that begins in glial cells (i.e., cells that surround and support nerve cells and includes oligodendrocytes, astrocytes, microglia, and ependymal cells). Gliomas are particularly serious in terms of both incidence and malignancy, and are classified into seven or more types such as glioblastoma and anaplastic astrocytoma according to their detailed pathological tissue type. Disease stage (tumor size, presence of distal metastasis) and histological malignancy are used when determining the degree of malignancy of primary brain tumors. Histological malignancy is classified into four levels, i.e., G1 to G4 according to the Guidelines for the Treatment of Brain Tumors ((2002) Kanehara & Co., Ltd.), and these correspond to WHO1 to WHO4, respectively. The larger the number, the higher the degree of malignancy. For example, the malignancy of glioblastoma is G4 (WHO4), while the malignancy of anaplastic astrocytoma is G3 (WHO3), and both G3 and G4 are classified as malignant. Thus, according to some embodiments, the methods of this invention target malignant gliomas. In other embodiments, the invention targets glioblastoma multiforme. In further embodiments, the present invention is extended to include the treatment of other gliomas including, but not limited to, anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor.

Subjects benefiting from treatment according to the invention include subjects with a glioma, or subjects suspected of having a glioma, as evidenced by the presence of headaches, nausea and vomiting, seizures, loss of vision, pain, weakness, numbness in the extremities, and/or cranial nerve disorders as a result of increased intracranial pressure. In particular embodiments, the glioma being treated is glioblastoma multiforme. In accordance with this embodiment, the glioblastoma multiforme can be in the brain or spinal cord.

As used herein, treatment of cancer encompasses either reducing the growth of a tumor in the subject, reducing the clinical symptoms associated with tumor growth in the subject, and/or increasing survival time as compared to a subject not receiving treatment. For the purposes of the present invention, "treatment" refers to both therapeutic treatment and prophylactic or preventative measures. As such, those in need of treatment include those already with the disorder as well as those prone to have the disorder (e.g., by genetic predisposition or exposure to carcinogenic agents). Subjects who can be treated in accordance with the present invention include mammals, such as humans, domestic and farm animals, and zoo, sports, or pet animals, e.g., dogs, horses, cats, cows, etc. Preferably, the mammal herein is human.

In human, microRNA-10 gene has been duplicated and is expressed in the form of two variants known as miR-10a and miR-10b, which are located on different chromosomes; miR-10a is located between HOX4B and HOX5B on 17q21, while miR-10b is located between HOXD4 and HOXD8 on 2q31.1. Accordingly, for the purposes of the present invention a miR-10 antagonist refers to an agent that inhibits the expression or activity of a product of one or both of the microRNA-10 genes. Products of the human miR-10 genes include pre-miR-10a (5'-GAU CUG UCU GUC UUC UGU AUA UAC CCU GUA GAU CCG AAU UUG UGU AAG GAA UUU UGU GGU CAC AAA UUC GUA UCU AGG GGA AUA UGU AGU UGA CAU AAA CAC UCC GCU CU-3'; SEQ ID NO:1); mature miR-10a (5'-UAC CCU GUA GAU CCG AAU UUG UG-3'; SEQ ID NO:2); pre-miR-10b (5'-CCA GAG GUU GUA ACG UUG UCU AUA UAU ACC CUG UAG AAC CGA AUU UGU GUG GUA UCC GUA UAG UCA CAG AUU CGA UUC UAG GGG AAU AUA UGG UCG AUG CAA AAA CUU CA-3'; SEQ ID NO:3); and mature miR-10b (5'-UAC CCU GUA GAA CCG AAU UUG UG-3'; SEQ ID NO:4). Agents which antagonize miR-10 activity or expression include antisense, ribozyme, inhibitory RNA, or small organic molecule known in the art or identified in screening assays. For example, an antisense 2'-O-methyl oligonucleotide molecule complementary to the longest form of the miR-10a or miR10b can be designed to specifically inactivate miR-10 activity in human cells (Meister, et al. (2004) *RNA* 10 (3) 544-550; Hutvágner, et al. (2004) *PLoS Biol.* 2 (4):e98). Alternatively, ANTI-MIR™ miRNA Inhibitors (Ambion) for miR-10a (product ID AM10787) and miR-10b (product ID AM12387) can be commercially obtained. Use of an miR-10 antagonistic compound will desirably reduce the expression or the activity of the microRNA by 10%, 20%, 30%, 40%, 50%, 60%, 70%, 80%, 90% or 100%. Such decreases can be monitored by detecting the level of miR-10a, miR-10b, or target mRNA or detecting the level of the protein product translated from the target mRNA and comparing said levels with those in control cells not contacted with the miR-10 antagonist. In one embodiment, the microRNA-10 antagonist specifically antagonizes miR-10a, i.e., it fails to antagonize miR-10b. In another embodiment, the microRNA-10 antagonist specifically antagonizes miR-10b, i.e., it fails to antagonize miR-10a. In other embodiments, the microRNA-10 antagonist antagonizes both miR-10a and miR-10b.

As indicated, the present invention also embraces the use of agents that increase the expression or activity of HOXD10, ZMYND11 and/or RB1CC1, referred to herein as activators, to reverse the transformed status of glioma tumor cells, induce neural cell differentiation, and prevent and/or treat glioma. Activators of the invention include nucleic acid molecules, proteins or small molecules that increase the expression or activity of HOXD10, ZMYND11 and/or RB1CC1. For example, nucleic acids encoding HOXD10, ZMYND11 or RB1CC1 can be used to increase expression. Said nucleic acids can be provided to a cell or subject as naked DNA, in expression vectors (e.g., adenoviral, adeno-associated viral, or lentiviral vectors), or in carriers such as liposomes routinely used in the art to facilitate the delivery and expression of nucleic acids in vivo. For example, HoxD10 has been shown to inhibit proliferation and tumorigenicity of GH4 pituitary lactotrope tumor cells when delivered via an adenovirus/adeno-associate hybrid virus (Cho, et al. (2008) *Biochem. Biophys. Res. Commun.* 371 (3):371-4). Alternatively, HOXD10, ZMYND11 or RB1CC1 can be provided to a cell or subject in the form of a purified protein prepared and isolated by conventional recombinant protein expression technologies. Desirably, an activator of the invention increases the expression or activity of HOXD10, ZMYND11 or RB1CC1 by at least 10%, 20%, 30%, 40%, 50%, 60%, 70%, 80%, 90% or 100% as compared to cells or subjects not contacted with the activator.

Effective amounts of antagonists and activators disclosed herein will depend upon the mode of administration, frequency of administration, nature of the treatment, age and condition of the individual to be treated, and the type of pharmaceutical composition used to deliver the antagonist or activator into a living system. While individual doses can vary, optimal ranges of effective amounts can be determined by one of ordinary skill in the art. For example, the safe and effective dosages identified in clinical trials can be considered when selecting dosages for treatments according to the present invention.

Antagonists and activators used in the methods of the present invention can be administered alone or as a pharmaceutical composition, which includes the compound(s) and a pharmaceutically-acceptable carrier. A pharmaceutical composition can include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

Antagonists and activators of the invention, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, such as, that of the nose, throat, and/or bronchial tubes (i.e., inhalation).

For most therapeutic purposes, an antagonist or activator of the invention can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compound(s) of the present invention and a carrier, for example, lubricants and inert fillers such as, lactose, sucrose, or cornstarch. In another embodiment, compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of an antagonist or activator of the invention can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, an antagonist or activator of the invention in solution or suspension may be packaged in a pressurized aerosol container together with suitable propellants, for example, hydrocarbon propellants like propane, butane, or isobutane with conventional adjuvants. The agent of the present invention also can be administered in a non-pressurized form such as in a nebulizer or atomizer.

For transdermal routes, an antagonist or activator of the invention is present in a carrier which forms a composition in the form of a cream, lotion, solution, and/or emulsion. The composition can be included in a transdermal patch of the matrix or reservoir type as are conventional in the art for this purpose.

It is also contemplated that administration of an antagonist or activator of the invention can be carried out in combination with other suitable therapeutic treatments which are useful for treating glial tumors. For example, an antagonist or activator of the invention can be combined with surgery, radiation therapy, and/or chemotherapy in the treatment of a glioma. Examples of chemotherapeutic agents which can be used in a combination treatment include, but are not limited to, temozolomide (TEMODAR; Schering Plough), irinotecan (CAMPTOSAR; Rhone Puolenc Rorer), carboplatin (PARAPLATIN; Bristol-Myers Squibb), oxaliplatin (ELOXATIN; Sanofi-Aventis), nitrosoureas, lomustine (CEENU; Bristol-Myers Squibb), vincristine (ONCOVIN; Gensia Sicor), vinblastine (VALBAN; Gensia Sicor), procarbazine (MATULANE; Sigma-tau), EGF receptor blockers such as cetuximab (ERBITUX; Imclone Systems), pertuzumab (OMNITARG, Genentech), erlotinib (TARCEVA, OSI), gefitinib (IRESSA, AstraZeneca) and imatinib mesylate (GLEEVEC, Novartis), multi-targeted tyrosine kinase inhibitors such as sorafenib (NEXAVAR, Bayer) or sunitinib malate (SUTENT, Pfizer). Additional therapeutics useful in the method of the invention include sirolimus (RAPAMUNE; Wyeth), RAD001 (Novartis), Sutan, Divalproes (DEPAKOTE; Abbott), and p13K and AKT inhibitors.

The invention is described in greater detail by the following non-limiting examples.

EXAMPLE 1

Role of miR-10a and miR-10b in GBM Oncogenesis

MiR-10a and miR-10b are candidate oncogenic microRNAs in GBM that are highly up regulated. To demonstrate that these microRNAs are involved in the initiation and/or progression of GBM, miR-10a and miR-10b expression in human GBM cells was analyzed. Based upon northern blot analysis, miR-10a and miR-10b were shown to be expressed in primary human GBM samples (2H, 4A10 and 64A44) when compared to normal brain tissue (NB1 and NB2). For this analysis, total RNA was isolated from the above-referenced samples by conventional methods and 20 µg of total RNA was loaded in each well. U6 loading controls were included for each blot.

Figure 1B:
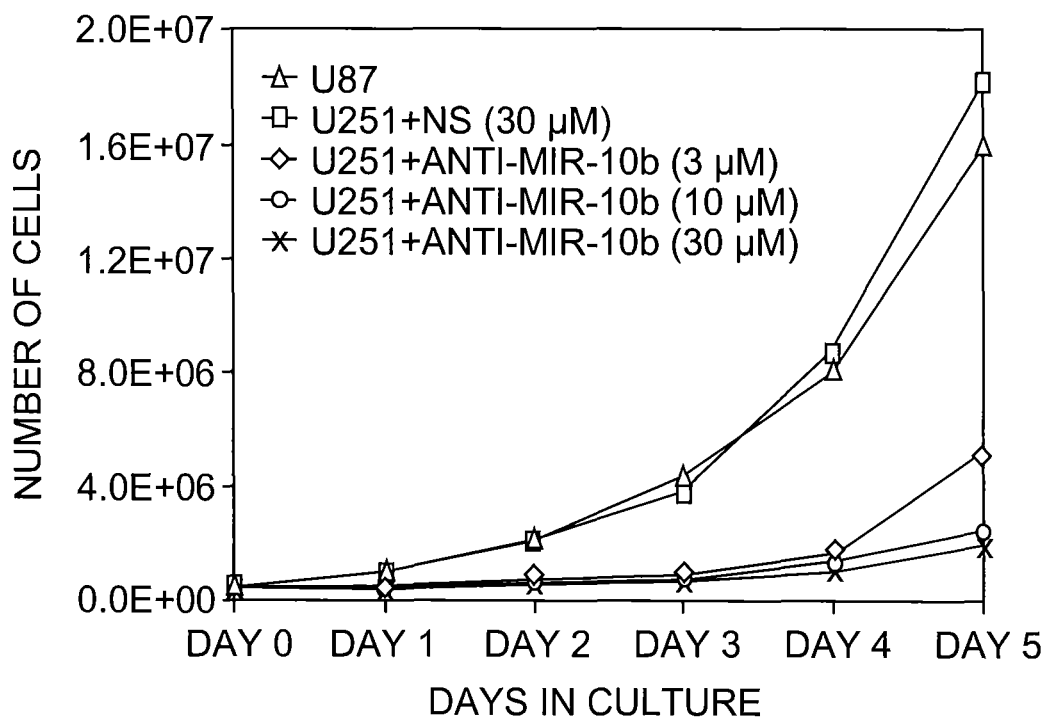

Toward demonstrating the use of anti-mir10a and anti-mir10b in targeting glioma tumor cells, miR-10a or miR-10b expression was knocked down using 2'-O-methyl-modified oligonucleotides complementary to miR-10a or miR-10b in human GBM-derived cell line U87. Specifically, U87 cells were transiently transfected with anti-mir10a (30 µM) or anti-mir10b (30 µM) and total RNA samples were collected at 24, 48 and 72 hours post transfection to determine miR-10a and miR-10b expression. A non-specific scrambled anti-miR inhibitor was used as a negative/toxicity control. FAM dye-labeled anti-miR non-specific inhibitor was used to determine transfection efficiency. This analysis indicated that anti-mir10a and anti-mir10b significantly decreased expression of miR-10a and mir10b, respectively. Accordingly, it was subsequently determined how the loss of function of these potentially oncogenic microRNAs affects the proliferation and most critically the oncogenic characteristics of the GBM cell lines. For this analysis, U251 or U87 cells were cultured in either medium only, non-specific anti-mir control (30 µM) or anti-miR-10a or anti-miR-10b (3, 10 and 30 µM). The growth curves shown in FIG. 1 demonstrate that anti-miR-10a and anti-miR-10b treatment inhibited the proliferation of GBM cells lines in vitro. In addition, suppression of miR-10a or miR-10b was shown to lead to disruption of anchorage-independent growth of GBM cell lines (Table 1).

TABLE 1

| Treatment of Cells | Number of Colonies Formed | | |
|---|---|---|---|
| | $1 \times 10^4$ Cells Plated | $1 \times 10^4$ Cells Plated | $1 \times 10^4$ Cells Plated |
| Untreated U87 Cells | 110 | 240 | 461 |
| U87 + Negative/Toxicity Control (30 µM) | 126 | 278 | 459 |
| U87 + Anti-miR-10a | 43 | 104 | 186 |
| U87 + Anti-miR-10b | 37 | 146 | 299 |
| Untreated Neural Stem Cells | 0 | 0 | 0 |

Cells were treated with anti-miR-10a (30 µM) or anti-miR-10b (30 µM) for 72 hours and plated on soft agar in 6-well plates. A non-specific (NS) scrambled anti-miR inhibitor was used as a negative/toxicity control for transfection and normal neural stem cells were used as a negative control for growth in soft agar. Untreated U87 cells were the positive control. Colony numbers represent one well of a 6 well plate and the numbers are averages of 6 wells per condition.

Figure 2A:
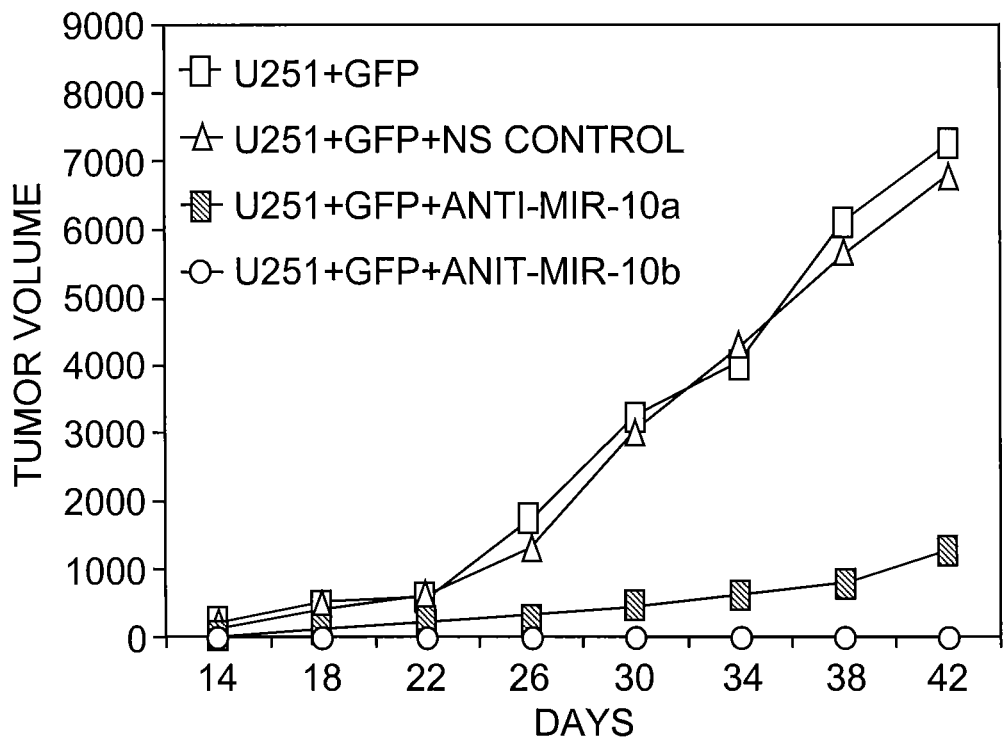
FIG. 2 shows that down regulation of miR-10a or miR-10b reduces or completely ablates xenograft growth in vivo. Shown are graphs of tumor volume (mm$^3$) of U251 (FIG. 2A) or U87 (FIG. 2B) xenografts in mice. U251 and U87 cells were treated for 72 hours with either anti-miR-10a, anti-miR-10b or a non-specific (NS) scrambled anti-miR inhibitor (30 µM) before injection into nude mice. Tumors were measured every four days starting at day 10 post-injection. The data are representative of three independent, completed experiments and one ongoing experiment.
Figure 2B:
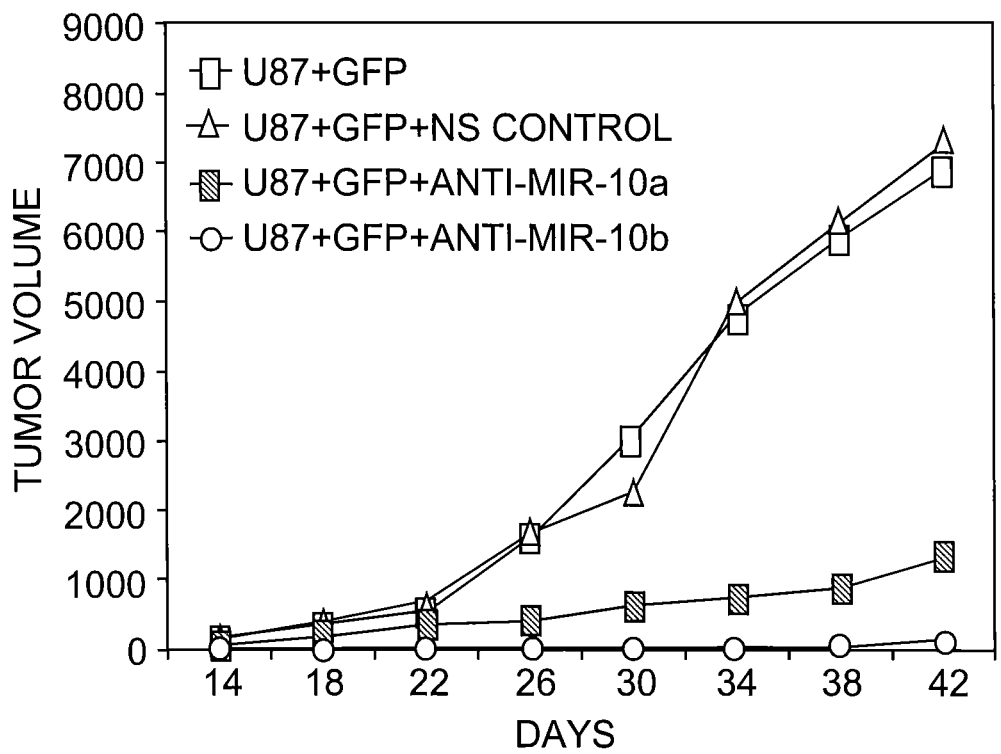

To demonstrate the in vivo effects of down-regulating miR-10a and miR-10b, a GBM xenograft model in immune-deficient nude mice was employed. U251 or U87 cells were treated for 72 hours with either anti-miR-10a, anti-miR-10b or a non-specific (NS) scrambled anti-miR inhibitor (30 µM) before being injecting into nude mice. The NS anti-miR inhibitor was used as a negative/toxicity control for transfection while untreated cells were the positive control. Cells ($5\times10^6$) were injected subcutaneously into nude mice (n=5 per group). Tumors were measured every 4 days starting at day 10 post-injection. Normally these cell lines give rise to large tumors in nude mice that can be detected using the Xenogen Imaging system. In anti-miR-10a treated groups, only 3 out of the 5 nude mice developed smaller tumors for both U251 as well as U87 xenografts. Tumor growth was completely ablated in anti-miR-10b-treated mice. Northern blot confirmed suppression of miR-10a and miR-10b in U251 and U87 cells that had been treated for 72 hours with the respective anti-mirs (30 µM) and injected into mice. The results presented in FIG. 2 show that down regulation of miR-10a or miR-10b reduced or completely ablated xenograft growth in vivo.

To further investigate the in vivo effects of miR-10a and miR-10b oncogenesis, miR-10a and/or miR-10b can be over-expressed in murine neural stem cells, wherein it is expected that overexpression of these microRNAs by conventional recombinant methods (e.g., as pre-mirs that will result in mature microRNAs) will lead to the transformation of the neural stem cells and growth in soft agar in which they are normally unable to grow.

EXAMPLE 2

Identification of Specific Targets of miR-10a and miR-10b and the Role of the Same in Regulating Oncogenic Processes By comparing gene expression data from primary GBM and normal brain tissue with miR-10a and miR-10b levels, as well as using MiRanda target prediction algorithm associated with the Sanger MIRBASE, ZMYND11 (Zinc finger, MYND domain containing 11), RB1CC1 (RB1-inducible coiled-coil 1) and HOXD10 were identified as potential targets of mirs-10a and miR-10b. In this respect, down-regulation of miR-10b in GBM cell lines was shown to increase one of these targets, namely HoxD10. It is expected that down regulating miR-10a and miR-10b expression will likewise result in an increase in the expression of ZMYND11 and RB1CC1 in GBM cell lines, e.g., as determined by qRT-PCR and western blot analyses. Moreover, it is expected that overexpression of any one, or combination of, HoxD10, ZMYND11 and RB1CC1 may modulate differentiation and/or angiogenesis of GBM lines. For example, overexpression may actually reverse the transformed status of GBM lines rendering them non-oncogenic (e.g., as determined by growth in soft agar or the GBM xenograft model).

To further analyze the role of ZMYND11, HoxD10 and RB1CC1 in human GBM pathology, it can be determined, e.g., whether overexpression of ZMYND11 and RB1CC1 leads to induction of their downstream target RB1 (a tumor suppressor), which, in turn, could potentially lead to a reversal of transformed status. In similar analysis, expression of markers of neural cell differentiation can be analyzed in GBM cell lines overexpressing HoxD10.

EXAMPLE 3

Comparisons Between Stem Cell-Like Tumor Initiating Cells and Normal Neural Stem Cells To gain a better understanding of GBM pathobiology, the sequence of events that normal cells undergo to become oncogenic is analyzed. This includes, determining the similarities and differences between stem cell-like tumor initiating cells and normal neural stem cells, and whether these characteristics change as tumors evolve. Moreover, it is determined whether microRNAs play a role in initial transforming events in GBM pathology and whether normal brain-derived neural stem cells (NSCs) share distinct intrinsic properties with tumor initiating cells in GBMs.

What is claimed is:

1. A method for decreasing glial tumor cell proliferation comprising contacting a glial tumor cell with an effective amount of a microRNA-10 antagonist, thereby decreasing the proliferation of the glial tumor cell as compared to a control.

2. The method of claim 1, wherein the glial tumor cell is an astrocytoma tumor cell, ependymal tumor cell, glioblastoma multiforme tumor cell, or primitive neuroectodermal tumor cell.

3. A method for treating glioma comprising administering to a subject in need thereof an effective amount of a microRNA-10 antagonist, thereby treating the subject's glioma.

4. The method of claim 3, wherein the glioma is an astrocytoma, ependymal tumor, glioblastoma multiforme, or primitive neuroectodermal tumor.

5. The method of claim 4, wherein the glioblastoma multiforme is located in the brain of the subject.

6. The method of claim 4, wherein the glioblastoma multiforme is located in the spinal cord of the subject.

7. The method of claim 3, wherein the subject is a human subject.

* * * * *